United States Patent [19]

Scoggins

[11] 4,125,373

[45] Nov. 14, 1978

[54] MEASUREMENT OF TRACE ETHYLENE GLYCOL IN OIL

[75] Inventor: Myles W. Scoggins, Bartlesville, Okla.

[73] Assignee: Phillips Petroleum Company, Bartlesville, Okla.

[21] Appl. No.: 811,357

[22] Filed: Jun. 29, 1977

[51] Int. Cl.$^2$ ............... G01N 21/26; G01N 31/22; G01N 33/28
[52] U.S. Cl. ..................... 23/230 HC; 23/230 M; 252/408
[58] Field of Search ......... 23/230 R, 230 M, 230 HC; 252/408

[56] References Cited

U.S. PATENT DOCUMENTS

| | | | |
|---|---|---|---|
| 2,209,764 | 7/1940 | Cassen et al. | 23/230 R |
| 3,544,275 | 12/1970 | Habermas et al. | 23/230 R |
| 3,635,677 | 1/1972 | Drake, Jr. et al. | 23/230 R |
| 3,645,696 | 2/1972 | Iannacone et al. | 23/230 R X |
| 3,734,358 | 1/1974 | Drake, Jr. | 23/253 TP |
| 3,915,638 | 10/1975 | Viccaro et al. | 23/230 M |

OTHER PUBLICATIONS

The 3-Methyl-2-benzothiazolone Hydrazone Test, Anal. Chem., vol. 33, No. 1, Jan. 1961, pp. 93-96.
ASTM Method D-2982-73, Detecting Glycol Based Antifreeze in Used Lubricating Oils.
Increasing Sensitivity of MBTH Test for Analysis of Alphatic Aldehydes in Air, Anal. Chem. vol. 36, 3/1964, pp. 679-681.

*Primary Examiner*—Morris O. Wolk
*Assistant Examiner*—Michael S. Marcus

[57] ABSTRACT

A method for determining ethylene glycol in motor oil in the range of about 10 to about 100 parts per million (ppm) in which ethylene glycol is extracted from an oil sample using water as extractant, the extracted ethylene glycol is oxidized with trisodium paraperiodate to form formaldehyde, the formaldehyde is condensed with 3-methyl-2-benzothiozilinone hydrazone hydrochloride (MBH), and ferric chloride then added to form a brilliant blue dye solution which indicates the presence initially of ethylene glycol. In a technique adapted for laboratory use the absorbance of the blue dye solution is measured spectrophotometrically at 630 nanometers (nm) and the measured absorbance is translated to a calibration of concentration of ethylene glycol in the oil sample.

5 Claims, No Drawings

MEASUREMENT OF TRACE ETHYLENE GLYCOL IN OIL

BACKGROUND OF THE INVENTION

This invention relates to the analysis of components of an oil composition. In one of its aspects this invention relates to the extraction of components from an oil composition. In another of its aspects this invention relates more particularly to the determination of the amount of ethylene glycol in motor oil. In still another of its aspects this invention relates to the oxidation of ethylene glycol to form formaldehyde. In still another of its aspects this invention relates to a method for determining the amount of formaldehyde in a composition by spectrophotometric methods.

In one of its concepts this invention relates to a method for converting one chemical compound into another chemical compound for which an advantageous analysis method exists. In a more specific concept the invention relates to quantitative conversion of ethylene glycol to formaldehyde with subsequent quantitative conversion of formaldehyde to a blue dye solution so that the spectrophotometric absorbance of the blue dye solution can be calibrated to the amount of ethylene glycol.

The determination of trace concentrations of ethylene glycol in used motor oil has proved to be a difficult task. Final determination techniques either by gas chromatography or by using chemical methods all require removal of the ethylene glycol from the oil before the final determination. Until recently this required the extraction of fairly large oil samples to determine low concentrations of ethylene glycol.

After extraction of the ethylene glycol from oil, the method most commonly used for determining the concentration of ethylene glycol has been a chemical technique requiring oxidation using periodic acid which is a specific oxidant for compounds with hydroxyl groups on adjacent carbon atoms. Periodic acid oxidation of ethylene glycol results in rupture of carbon-carbon bonds to form formaldehyde. The amount of formaldehyde can then be determined spectrophotometrically as a colored dye after reaction with either chromatropic acid or p-fuchsin. The chromatropic acid technique is highly sensitive, but has the disadvantage of requiring concentrated sulfuric acid as solvent. p-Fuchsin must be decolorized with sulfurous acid prior to use and numerous oxidizing agents will regenerate the color.

Another procedure has recently been developed for determining trace concentrations of formaldehyde. In this method, the formaldehyde is condensed with 3-methyl-2-benzothiozilinone hydrazone (MBH) to form an intensely brilliant blue cationic dye. Initial experiments trying to adapt the formaldehyde-MBH condensation to be used with formaldehyde produced by periodic oxidation of ethylene glycol were unsuccessful due to interference in the condensation reaction by the excess periodate used as ethylene glycol cleaving agent. Potassium periodate in acid solution had been the cleaving agent commonly used, but gave such erratic and inconsistent results that the supposed reaction mechanism for producing the brilliant blue dye came under question. It was then discovered that trisodium paraperiodate, $Na_3H_2IO_6$, could be used as an effective oxidant for ethylene glycol and, at the same time, would not oxidize MBH and thereby interfere with its condensation with formaldehyde.

Experimental determinations of 10 to 100 ppm ethylene glycol in used motor oil had indicated that oxidation to formaldehyde followed by the MBH reaction technique has advantages over the current methods of analysis with respect to sensitivity and simplicity. This provides not only an accurate laboratory method for determining ethylene glycol in used motor oil, but also provides a test simple enough to be used in service stations and garages to determine whether there is ethylene glycol in a sample of motor oil from an automobile. The service station and garage testing will become of greater importance as recommendations for using automotive motor lubricants for up to 10,000 miles become more common.

It is therefore an object of this invention to provide a method for determining the presence of ethylene glycol in used motor oil in a range of about 10 to about 100 ppm. It is another object of this invention to provide a sensitive and simply operated method for determining the presence of ethylene glycol in automotive motor lubricants.

Other aspects, objects and the various advantages of this invention will become apparent upon reading this specification and the appended claims.

STATEMENT OF THE INVENTION

According to this invention a method is provided for determining the presence of ethylene glycol in motor oil. In this method a sample of motor oil is extracted using water as extractant, the water extractant and its contents are contacted with trisodium paraperiodate, this mixture is further contacted with 3-methyl-2-benzothiozilinone hydrazone hydrochloride, and ferric chloride is then added to form a blue dye solution which indicates that ethylene glycol was initially present in the oil sample. In this process the extracted ethylene glycol is oxidized by contact with trisodium paraperiodate to form formaldehyde, the formaldehyde is condensed by contact with MBH and ferric chloride added to form a blue dye solution.

In an embodiment of the invention the presence of ethylene glycol in a motor oil sample in the range of about 10 to about 100 ppm can be determined by spectrophotometric analysis of the absorbance of the blue dye prepared as described above with comparison of the absorbance data to a calibration curve prepared by oxidizing and reacting a series of solutions containing from 10 to 100 ppm ethylene glycol.

The following sequence of reactions probably occurs during the analysis:

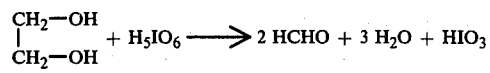

1.

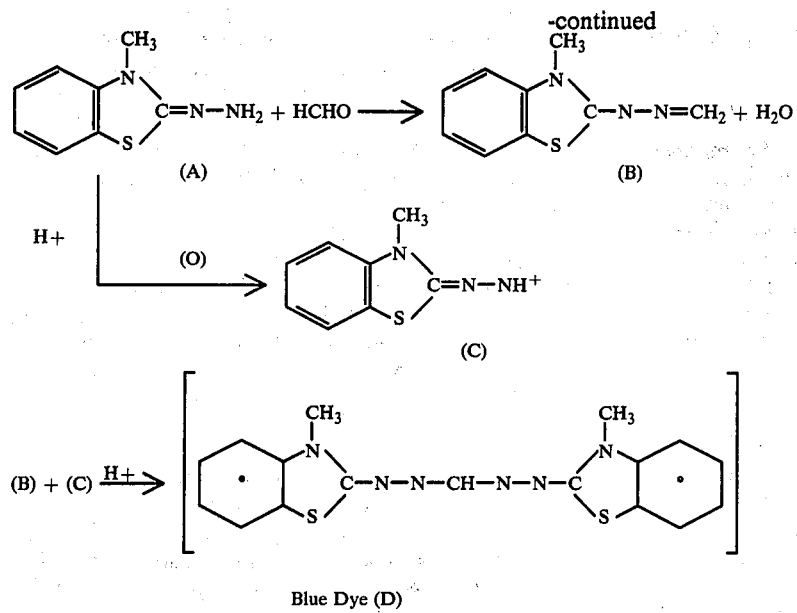

Blue Dye (D)

Following oxidation of ethylene glycol to formaldehyde, MBH is added to form the condensation product (B) in a fairly slow reaction. Excess MBH is rapidly oxidized with FeCl$_3$ to form product (C) which condenses with product (B) to form the brilliant blue cationic dye (D). The dye has a molar absorptivity of $9 \times 10^4$ 1/mol-cm (based on ethylene glycol) at its absorption maximum of 630 mm.

Because of the extremely high intensity of the blue cationic dye, oil samples of 0.1 to 0.5 grams are sufficient for analysis. This eliminates many of the problems associated with water extraction of large oil samples. Although unused motor oils can be easily extracted with water, it is difficult to extract used oil because of the ease with which emulsions form. Dilution of the oil with organic solvents fails to improve the situation. The high sensitivity of the MBH measuring technique favors the extraction of small oil samples. Oil samples of 0.1 to 0.5 grams can be weighed into glass vials, capped and after heating on a hot plate, the hot oil is spread over the inner surface of the vial by slowly rotating the hot vial. Addition of water to the vial results in a large oil-water interface. By keeping the vial and its contents warm and slowly agitating the vial, a continously renewed oil-water interface is achieved and ethylene glycol is extracted by a diffusion process. Heat is a major contributor to successful extraction. It has been found that agitation in a heated ultrasonic bath hastens extraction, but has the disadvantage of disintegrating the oil into finely divided droplets that remain suspended in the aqueous phase. The best precision in the extraction operation under laboratory conditions is obtained with initial agitation in a warm ultrasonic bath followed by slow rotation of the sample vials while hot for a total contact time of one hour. This achieves the same results as 24 hours of hot extraction.

For laboratory precision, it is necessary quantitatively to recover the small volume of extraction water. This can be accomplished by filtering the water-oil mixture through filter paper. The water rapidly passes through the paper while the oil remains on the paper. Most filter paper, regardless of the manufacturer, contains a substance that interferes with the analysis technique. Ethylene glycol-free water after passage through filter paper will give intensely brilliant blue solutions on analysis. It is, therefore, imperative that filter paper be thoroughly washed prior to filtration of the extraction water in this process.

In the oxidation of ethylene glycol with trisodium paraperiodate the oxidation can be carried out at ambient temperature and is essentially complete in about 30 minutes. Maximum sensitivity for reaction time of 30 minutes is obtained using a molar ratio of trisodium paraperiodate to ethylene glycol of approximately 6:1.

In the reaction of MBH with formaldehyde the final color intensity of the blue cationic dye is independent of the MBH concentration as long as MBH is present in excess, i.e., enough to undergo both the condensation reaction with formaldehyde and the oxidation reaction with FeCl$_3$ to form the final cationic dye. Excess MBH does not affect the final results. The amount of FeCl$_3$ has an effect in that the apparent color of the final solution can be changed from blue to a greenish-blue; however, the wavelength of maximum absorbance remains unchanged. The final color intensity reaches a maximum about 10 minutes after addition of FeCl$_3$ and is stable for at least an hour. If, after addition of MBH and FeCl$_3$ the aqueous solution is faintly turbid the presence of undissolved organic matter is indicated. Dilution of the aqueous solution with acetone will remove the turbidity.

EXAMPLE I

A 0.003 M solution of trisodium paraperiodate (G. Frederick Smith Chemical Co.) acidified with acetic acid to pH 5 was used as oxidant for ethylene glycol. Formaldehyde reagents were 0.7 W/V percent solution of 3-methyl-2-benzothiozilinone hydrazone hydrochloride (Eastman No. 8443) and 0.2 W/V percent solution of FeCl$_3$·6H$_2$O. Two dram, screw cap, specimen vials were used for extraction tubes. Absorbance measurements were made on a Cary Model 14 spectrophotometer.

0.1 to 0.5 g oil was weighed into a 2 dram vial. The vial was capped securely and warmed with its contents to 60°–70° C. The vial was rotated to spread the hot oil over the inner glass surface and about 3 to 4 ml of warm water were added. The vial was placed in a warm ultrasonic bath for 15 minutes and the extraction was completed by slowly rotating or shaking the vial and its contents for an additional 45 minutes with intermittant heating to keep the mixture warm. A filter assembly was prepared and conditioned by placing a 9-cm sheet of number 41 Whatman filter paper in a funnel and washing with at least 100 ml of water. The wash water was discarded. The warm oil-water mixture was filtered through the conditioned assembly and the water extract was collected in a 100 ml volumetric flask. The vial was rinsed three times with 3 ml portions of warm water the rinse water was filtered and combined with the extract in the 100 ml volumetric flask.

4 ml of trisodium paraperiodate solution were added, mixed and allowed to react for 30 minutes at room temperature. 2 ml of MBH solution was added, mixed and allowed to react for 20 minutes. 30 ml FeCl$_3$ solution was added and after 5 minutes the solution was diluted to volume with acetone. Blank determinations were made starting with the addition of trisodium paraperiodate.

Absorbance of the blue dye vs. the reagent blank was measured in 1-cm cells at 630 nm. The absorbance measurement was compared to a previously prepared calibration curve to ascertain the concentration of ethylene glycol in the oil sample.

containing 53.3 ppm of ethylene glycol, was analyzed nine times and gave a standard deviation of 1.75 ppm.

Used oil G, analyzed to contain 110 ppm ethylene glycol, was fortified to contain 229 ppm. Analysis of the fortified blend yielded 230 ppm ethylene glycol with a standard deviation of 7.5 ppm.

The gas chromatographic analyses were performed on water extracts of much larger oil samples. Blend D represents about the lowest concentration of ethylene glycol that can be accurately determined by chromatographic analysis. Blends H and J were found to contain 27 and 25 ppm, respectively, by the spectrophotometric procedure while none was detected by gas chromatography. It appears that the lower detection limit by gas chromatography is approximately the middle of the spectrophotometric technique range.

EXAMPLE II

In a procedure developed for determining the presence of ethylene glycol in used oil the following example has been calculated. About 10 cc of oil sample is placed in a 25 cc screw cap, glass container. The container is capped securely and warmed with its contents to about 60°–70° C. The container is rotated to spread the hot oil over the inner glass surface and about 3 or 4 ml of warm water are added. The extraction is com-

TABLE I.
EXTRACTION OF ETHYLENE GLYCOL FROM USED OIL

| Run | Grams Oil | Treatment | Ethylene Glycol, ppm |
|---|---|---|---|
| 1 | 0.2122 | Slow Roll, 1 Hour, Room Temperature | 71.8 |
|   | 0.2213 |  | 54.6 |
|   | 0.2002 | Slow Roll, 1 Hour, 60–70° C | 91.9 |
| 2 | 0.2070 |  | 92.1 |
|   | 0.1980 | Ultrasonic Bath (60° C), 15 min., | 113.6 |
| 3 | 0.2181 | Slow Roll, 45 min., (60–70° C) | 112.6 |
|   | 0.1999 | Ultrasonic Bath (60° C), | Oil dispersed in aqueous solution. Light scatter prevents measurement. |
| 4 | 0.2075 | 1 Hour |  |
|   | 0.2085 | Ultrasonic Bath, Room Temperature, 1 Hour | 50.3 |
| 5 | 0.2258 |  | 48.0 |
|   | 0.1927 | Slow Roll, 24 hours, 65–70° C | 107.5 |
| 6 | 0.1899 |  | 108.7 |
|   | 0.2530 |  | 110.4 |

It is apparent from these experiments that heat is the major contributor to successful extractions.

TABLE II.
RECOVERY OF ETHYLENE GLYCOL FROM OIL

| Sample | Added | Found, ppm This Method | GC |
|---|---|---|---|
| New Oil Blends |  |  |  |
| A | 14.3 | 12.8 |  |
| B | 25.2 | 24.0 |  |
| C | 45.7 | 42.3 |  |
| D | 53.3 | 54.9* | 45 |
| E | 68.5 | 68.8 |  |
| F | 125 | 134 | 105 |
| Used Oils |  |  |  |
| G | — | 110 |  |
| G | 119 | 230 | 170 |
| H | — | 27 | None Detected |
| J | — | 25 | None Detected |
| K | — | 675 | 604 |

*Standard Deviation (N = 8) = 1.75

The results shown in Table II indicate the accuracy and precision of the procedure of this invention. Six blends of new oil in the 15 to 125 ppm range gave results with an average recovery of 98.1 percent. Blend D, pleted by rotating the capped container and its contents for about an hour, preferably in a mechanical device, with intermittant heating to keep the mixture warmed to about 60° to 70° C. The container is then let stand to obtain separation of the oil and water. A portion of the water phase, after separation, is removed into another small container using a medicine dropper. To this is added about eight drops of trisodium paraperiodate solution which is allowed to mix and react for about 30 minutes at room temperature. To this is added about four drops of MBH solution which is allowed to mix and react for about 20 minutes. About 30 ml of FeCl$_3$ solution is then added and the appearance of a blue or bluegreen coloration indicates the presence of ethylene glycol in the oil.

I claim:

1. A method for determining the presence of ethylene glycol in motor oil said method comprising:
    (1) extracting a sample of said motor oil using water as extractant, (2) contacting the water extractant and its extracted contents with trisodium paraperiodate,
(3) contacting the extractant and its extracted contents from step 2 with 3-methyl-2-benzothiozilinone hydrazone hydrochloride, and
(4) contacting the mixture of step 3 with ferric chloride thereby forming a blue dye solution indicating that ethylene glycol was initially present in the oil sample.

2. A method of claim 1 for detecting the presence of ethylene glycol in a motor oil sample in the range of about 10 to 100 ppm comprising analyzing the absorbance of the blue dye solution spectrophotometrically.

3. A method of claim 2 wherein the spectrophotometric analysis of the absorbance in the blue dye is compared to a calibration curve prepared by oxidizing and reacting a series of solutions containing from 10 to 100 ppm ethylene glycol.

4. A method for determining the presence of ethylene glycol in motor oil said method comprising:
(1) placing about 10 cc of oil sample in a container, securely capped and warmed to about 60°–70° C.,
(2) adding about 3 to about 4 ml of warm water with rotation of the container to spread the hot oil over the container's surface,
(3) continuing rotation of said container and its contents for a time sufficient for extraction of ethylene glycol from the oil with sufficient heating to maintain the mixture at about 60° to about 70° C.,
(4) allowing the separation of the oil and water,
(5) removing a portion of the water phase into a small container, then
(6) adding to the removed portion of the water phase trisodium paraperiodate solution and mixing and reacting at room temperature for a time sufficient to produce formaldehyde,
(7) adding to this mixture 3-methyl-2-benzothiozilinone hydrazone hydrochloride solution with mixing for a time sufficient for condensing 3-methyl-2-benzothiozilinone hydrazone hydrochloride with formaldehyde, and
(8) adding $FeCl_3$ solution to the mixture of step 7 thereby producing a blue or bluegreen coloration to indicate the presence of ethylene glycol initially in the oil sample.

5. A method for detecting the presence of ethylene glycol in a motor oil sample in the range of about 10 to 100 ppm said method comprising:
(1) weighing about 0.1 to about 0.5 grams of oil into a vial,
(2) warming said vial and its contents to about 60°–70° C. while rotating said vial,
(3) adding about 3 to about 4 ml of warm water with continued rotation or shaking of said vial with intermittent heating to maintain the temperature at about 60°–70° C. for a time sufficient for extraction of ethylene glycol with water,
(4) filtering the mixture through a washed paper filter,
(5) collecting the extractant in a container, then
(6) adding about 4 ml of trisodium paraperiodate solution with mixing at room temperature for a time sufficient for reaction to produce formaldehyde,
(7) adding about 2 ml of 3-methyl-2-benzothiozilinone hydrazone hydrochloride with mixing and allow to react for a time sufficient to condense 3-methyl-2-benzothiozilinone hydrazone hydrochloride with formaldehyde,
(8) adding $FeCl_3$ solution and allowing to form a blue dye solution,
(9) measuring the absorbance of the blue dye solution, and
(10) comparing the absorbance measurement with previously prepared standards to ascertain the concentraction of ethylene glycol in the oil sample.

* * * * *